(12) United States Patent
Diviesti et al.

(10) Patent No.: US 11,319,131 B2
(45) Date of Patent: May 3, 2022

(54) STERILIZATION POUCH

(71) Applicant: Amcor Flexibles, Inc., Mundelein, IL (US)

(72) Inventors: Katherine Isobel Diviesti, Arlington Heights, IL (US); Jesse Blake, Rochester Hills, MI (US); Adam Jan Dworak, Northbrook, IL (US)

(73) Assignee: Bemis Company, Inc., Neenah, WI (US)

( * ) Notice: Subject to any disclaimer, the term of this patent is extended or adjusted under 35 U.S.C. 154(b) by 0 days.

(21) Appl. No.: 13/677,475

(22) Filed: Nov. 15, 2012

(65) Prior Publication Data
US 2014/0133785 A1 May 15, 2014

(51) Int. Cl.
*B65D 75/58* (2006.01)
*B65B 61/18* (2006.01)
(Continued)

(52) U.S. Cl.
CPC .......... *B65D 75/5894* (2013.01); *A61B 50/30* (2016.02); *A61F 13/0008* (2013.01); *A61F 13/00072* (2013.01); *A61F 15/001* (2013.01); *A61L 2/206* (2013.01); *A61L 2/26* (2013.01); *B65B 9/02* (2013.01); *B65B 61/182* (2013.01); *B65D 75/30* (2013.01); *A61B 2017/00526* (2013.01); *A61B 2050/314* (2016.02); *A61L 2202/181* (2013.01); *A61L 2202/24* (2013.01); *A61M 25/002* (2013.01); *B65B 55/10* (2013.01);
(Continued)

(58) Field of Classification Search
CPC ............. A61L 2202/21; A61L 2202/23; A61L 2202/24; A61L 2202/181; B65D 75/58; B65D 75/5855; B65D 75/5894; B61L 2202/18; B61L 2202/181; A61B 50/30; A61B 2050/314
USPC ........ 206/438, 439, 484.1, 484.2; 383/210.1, 383/210, 211
See application file for complete search history.

(56) References Cited

U.S. PATENT DOCUMENTS 3,685,720 A * 8/1972 Brady .......................... 206/439
3,761,013 A * 9/1973 Schuster ............. A61M 25/002
206/439

(Continued)

FOREIGN PATENT DOCUMENTS

EP 0 846 445 6/1998
JP H 06050611 7/1994
(Continued)

OTHER PUBLICATIONS

JP2010268967Translation.*
(Continued)

*Primary Examiner* — Jes F Pascua
*Assistant Examiner* — Nina K Attel (57) ABSTRACT

The invention provides a sterilizable pouch having at least one wall formed of a flexible film and including an opening formed therein for providing communication to an interior space of the package. A breathable material is disposed on an outer surface of the wall covering the opening. The breathable material is joined to the outer surface of the wall with a continuous heat seal. The flexible film forming the wall comprises a multilayer film having a peel feature that permits the breathable material to be peelably removed from the surface of the pouch.

22 Claims, 9 Drawing Sheets

(51) Int. Cl.
  *A61F 13/00*  (2006.01)
  *A61F 15/00*  (2006.01)
  *A61L 2/26*   (2006.01)
  *B65D 75/30*  (2006.01)
  *A61L 2/20*   (2006.01)
  *B65B 9/02*   (2006.01)
  *A61B 50/30*  (2016.01)
  *A61M 25/00*  (2006.01)
  *A61B 17/00*  (2006.01)
  *B65B 55/10*  (2006.01)

(52) U.S. Cl.
  CPC .... *B65D 2205/00* (2013.01); *F04C 2270/041* (2013.01)

(56) References Cited

U.S. PATENT DOCUMENTS

| | | | |
|---|---|---|---|
| 4,881,649 | A | 11/1989 | Hsu et al. |
| 5,551,781 | A * | 9/1996 | Wilkes ............... A61L 2/26 206/439 |
| 5,590,778 | A | 1/1997 | Dutchik |
| 5,773,136 | A | 6/1998 | Alder et al. |
| 5,965,254 | A * | 10/1999 | Christopherson et al. ... 428/349 |
| 5,976,299 | A | 11/1999 | Ivey |
| 5,997,968 | A | 12/1999 | Dries et al. |
| 6,080,456 | A | 6/2000 | Fonteyne |
| 6,117,505 | A | 9/2000 | Weiss et al. |
| 6,189,694 | B1 | 2/2001 | Weiss et al. |
| 6,231,975 | B1 | 5/2001 | Kong et al. |
| 6,234,310 | B1 | 5/2001 | Goldhaber |
| 6,251,489 | B1 | 6/2001 | Weiss et al. |
| 6,279,745 | B1 | 8/2001 | Huynen et al. |
| 6,451,426 | B2 | 9/2002 | Kong et al. |
| 6,632,313 | B2 | 10/2003 | Nickel et al. |
| 6,770,361 | B2 | 8/2004 | Kong |
| 6,828,019 | B2 | 12/2004 | Kong et al. |
| 6,893,672 | B2 | 5/2005 | Ingraham |
| 6,896,956 | B2 | 5/2005 | Kong |
| 6,960,392 | B2 | 11/2005 | Le Du et al. |
| 7,354,635 | B2 | 4/2008 | Malfait et al. |
| 7,434,372 | B2 | 10/2008 | Vanhamel et al. |
| 7,758,484 | B2 | 7/2010 | Peterson |
| 8,048,501 | B2 | 11/2011 | Singh |
| 8,062,723 | B2 | 11/2011 | Singh |
| 8,070,188 | B2 | 12/2011 | Cronley |
| 8,071,188 | B2 | 12/2011 | Singh |
| 2004/0115457 | A1 | 6/2004 | Kong |
| 2004/0166259 | A1 | 8/2004 | Merritt |
| 2005/0255980 | A1 | 11/2005 | Ventura et al. |
| 2011/0127188 | A1 | 6/2011 | Thompson et al. |
| 2011/0229372 | A2 | 9/2011 | Whitehead et al. |
| 2012/0247072 | A1 | 10/2012 | Romijn et al. |

FOREIGN PATENT DOCUMENTS

| | | |
|---|---|---|
| JP | 2001-524038 | 11/2001 |
| JP | 2003-211565 | 7/2003 |
| JP | 2007 276803 A | 10/2007 |
| JP | 2010268967 A * | 12/2010 |
| WO | WO-96/04178 | 2/1996 |
| WO | WO-98/45115 | 10/1998 |
| WO | WO-2011/038961 | 4/2011 |

OTHER PUBLICATIONS

International Search Report and Written Opinion for Application No. PCT/US2013/036687, dated Jul. 3, 2013.
International Preliminary Report on Patentability for Application No. PCT/US2013/036687 dated Feb. 19, 2015.
Office Action for corresponding European Application No. 13724924.9 dated Mar. 9, 2017.
Office Action for corresponding Japanese Application No. 2015-543030 dated Jan. 27, 2017.
International Search Report and Written Opinion for Application No. PCT/IB2016/057078, dated Feb. 22, 2017.
Second Written Opinion of the International Preliminary Examining Authority from International Application No. PCT/IB2016/057078, dated Oct. 20, 2017, 6 pages.
International Preliminary Report on Patentability (Chapter II) from International Application No. PCT/IB2016/057078, dated Dec. 6, 2017, 12 pages.
Office Action for corresponding European Application No. 13724924.9 dated Mar. 5, 2018, 6 pages.
Communication under Rule 71(3) for corresponding European Application No. 13724924.9 dated May 22, 2018, 69 pages.
Decision to Grant Patent for Japanese Application No. 2015-543030 dated Aug. 18, 2017.

* cited by examiner

STERILIZATION POUCH

FIELD

The present invention is directed to a package for sterilizing articles, and more particularly, a package for the packaging and sterilization of medical devices.

BACKGROUND

Sterilizable containers in the form of pouches or bags are popular vehicles for storing and transporting sterile medical devices, including instruments, dressings, drapes, etc. Such pouches often utilize heat-sealed transparent plastic sheets, for example low density polyethylene, positioned face-to-face and sealed around the common periphery. In particular, it is generally desirable to sterilize the medical instruments and devices after packaging and prior to being sent to the end user. Common forms of sterilization include irradiation; autoclaving, and treatment with a sterilizing gas, such as ethylene oxide. Typically, treatment with a sterilizing gas is used to sterilize many such instruments and devices. For example, one conventional form of package for sterilizing medical devices, such as a stent, comprises a polymeric sheet and a sheet of a porous, breathable material, such as TYVEK®, that are attached to each other along their peripheral edges to form seams defining a pouch. The breathable material is typically a sheet material that is a microbe barrier and is gas pervious.

Another common package for packaging of medical devices is a package in which the pouch includes an opening through which a sterilizing gas can be introduced into the interior space of the pouch. In this type of package, the access opening is covered by a porous breathable material that is permanently sealed to the outer surface of the pouch. These types of packages typically include a tear notch located at one end of the pouch that can be used to linearly tear the film and gain access to the contents of the pouch. A disadvantage that may be associated with this form of packaging is that the lack of aseptic presentation upon opening of the package.

In another common package, the pouch includes an access opening that is covered with a sealable strip, commonly referred to as a "header", made from a porous, breathable material that is sealed to one, or both, of the plastic sheets to cover the access opening. The header is often made from a porous breathable membrane and not only functions as a cover for the access opening, but also facilitates sterilizing the package contents. The porous characteristics of the breathable material allow a sterilizing medium, such as sterilizing gas (e.g., steam, ethylene oxide, etc.) to pass into and out of the pouch, while forming a sterile barrier against bacteria or other contaminants.

In order for the header to be easily removed to gain access to the opening, the breathable material is typically coated so that the breathable membrane is peelable from the surface of the package. Unfortunately, the presence of a coating results in a substantial decrease in the porosity, and hence breathability of the breathable material. This in turn results in longer sterilization times to ensure that an effective amount of sterilization gas is introduced into the package. In order to address this problem, packages have been developed in which the size of the opening is greatly increased to thereby improve the overall breathability of the package. However, such designs necessarily require an increased amount of breathable material in order to cover the opening, which results in higher production costs.

A further problem that has been associated with the use of a coated breathable material is the release of particulate matter from the coating itself, or from the breathable material as it is removed from the package. The release of such particulate matter can compromise the sterile field, and is therefore unacceptable. Regardless of the coating used, it has been a problem for package designers to select the proper coating that both retains the desired porosity of the header to allow sterilizing agent to be introduced at a desired rate, while also providing a good peelable seal between the header and the plastic sheet.

To address the issues with the use of coated breathable materials, U.S. Pat. No. 5,551,781 describes a package having an interlayer between the breathable material and access opening. The interlayer is applied to the opening, and the porous breathable material is then placed in contact with the interlayer. This design has many limitations including complicated processing and user complexity as well as increased production costs.

Such conventional packaging for surgery kits and other medical devices/instruments are generally considered inefficient and wasteful of material and labor. Accordingly, there is a need for a more cost and labor effective method for the packaging and sterilization of medical devices and instruments.

BRIEF SUMMARY

As briefly discussed above, commonly available sterilizable packages have many disadvantages that have not sufficiently been addressed by the prior art. In particular, it is noted that prior to the present disclosure, the inventors were unaware of any sterilizable package having a removable (e.g., peelable) breathable material adhered directly to the outer surface of a package in the absence of a coating. To this end, the inventors of the present disclosure have endeavored to develop a sterilizable package that overcomes the disadvantages of prior sterilizable packages.

The inventors of the present disclosure have now discovered that sterilizable packages in which an uncoated breathable material is directly adhered to an exterior surface of the sterilizable package may help overcome many of the problems of prior sterilizable packages. In particular, embodiments of the present invention are directed to sterilizable packages comprising front and back sheets of a flexible film are joined to each other along adjacent edges to define a pouch having an interior space for receiving an article therein. At least one of the front or back sheets includes an opening formed therein for providing communication between an exterior environment of the pouch and the interior space of the pouch. A breathable material is disposed on an outer surface of the wall covering the opening. The film in which the opening is formed includes a peel feature that permits the breathable material to be peelably removed from the pouch without tearing of the breathable material.

As explained in greater detail below, the peel feature may be provided by a multilayer film in which the outer layer of the film that is joined to the breathable material includes a modified chemistry, such as blend of incompatible polymers, so that the peel strength between the breathable material and the outer layer is less than 4 lbs./in. Access to the opening of the pouch can then be achieved by peeling the breathable material away from the outer surface of the pouch.

Alternatively, the peel feature may be provided by a multilayer film having an outer heat sealable layer defining an outer surface of the pouch, and an intermediate rupturable layer underlying the heat sealable layer. As discussed in greater detail below, the peel strength of the intermediate rupturable layer is less than the peel strength of the heat seal between the breathable material and the outer surface of the pouch. As a result, access to the opening, and hence, the contents of the pouch, can be gained by peeling back the breathable material which results in rupturing of the intermediate rupturable layer along the heat seal. In this way, pouches in accordance with the present invention provide a breathable membrane though which a sterilizing medium can be introduced into the pouch, as well as a peelable opening that can be used to remove sterilized articles from the pouch.

The inventors of the present invention have observed that attaching the breathable material to a film having a peel feature may provide several advantages and may also help overcome many of the disadvantages associated with prior art sterilizable packages.

One such advantage is that a peelable breathable material can be provided in the absence of having to use a coating on the breathable material in order to make the breathable material "peelable" from the surface of the pouch. Non-coated breathable material can be 60% or more, more porous in comparison to the same material when coated. As a result, the porosity and breathability of the breathable material is not reduced by the presence of the coating, which in turn, allows for a quicker gas exchange with the interior space of the pouch during sterilization. As such, embodiments of the present invention may help reduce the time needed to sterilize the contents of the pouch.

In addition, the inventors have observed that the use of a film having a peel feature may also help to reduce the amount of particulate matter (e.g., fibers and particles) created when handling the pouch, for example, during packaging, sterilizing, shipping, and removing the breathable material. In particular, it has been observed that the amount of particulate matter produced during removing of the breathable material may be significantly less in comparison to a peelable opening in which a coated breathable material, such as a coated TYVEK®, is heat sealed directly to the outer surface of the sheet material, or sealed to an additional intermediate layer. As such, embodiments of the present invention may help provide an improved aseptic presentation, which is particularly desirable in medical applications. For example, in embodiments of the present invention, a medical device may be removed from the pouch using aseptic technique into a sterile field, which in turn, may help reduce the need of a custom sterile wrap to protect the package from contamination.

Embodiments of the present invention may also help to provide for a more simplified manufacturing process. In contrast to the package described in U.S. Pat. No. 5,551,781, embodiments of the present sterilizable package do not require the presence of an intermediate peelable substrate disposed between the breathable material and the exterior surface of the sterilizable package. As a result, embodiments of the present invention provided for a more simplified and cost effective manufacturing process. As a further advantage, by incorporating a peel feature into the film, the peel function (e.g., peelability) of the breathable material can be adjusted depending on the intended application of the sterilizable package without altering the porosity of the breathable material.

In one embodiment, the breathable material comprises an uncoated fibrous material that is impervious to microorganisms, but pervious to gases. The breathable material overlies and covers the opening, and is preferably joined to an outer surface of the front or back sheet with a continuous heat seal.

After an article has been sealed in the pouch, a sterilizing medium, such as ethylene oxide, can be introduced into the interior space of the pouch through the breathable material.

Accordingly, it can be seen that embodiments of the claimed invention overcome many of the disadvantages associated with prior art sterilizable packages having an access opening that is covered with a removable breathable material.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
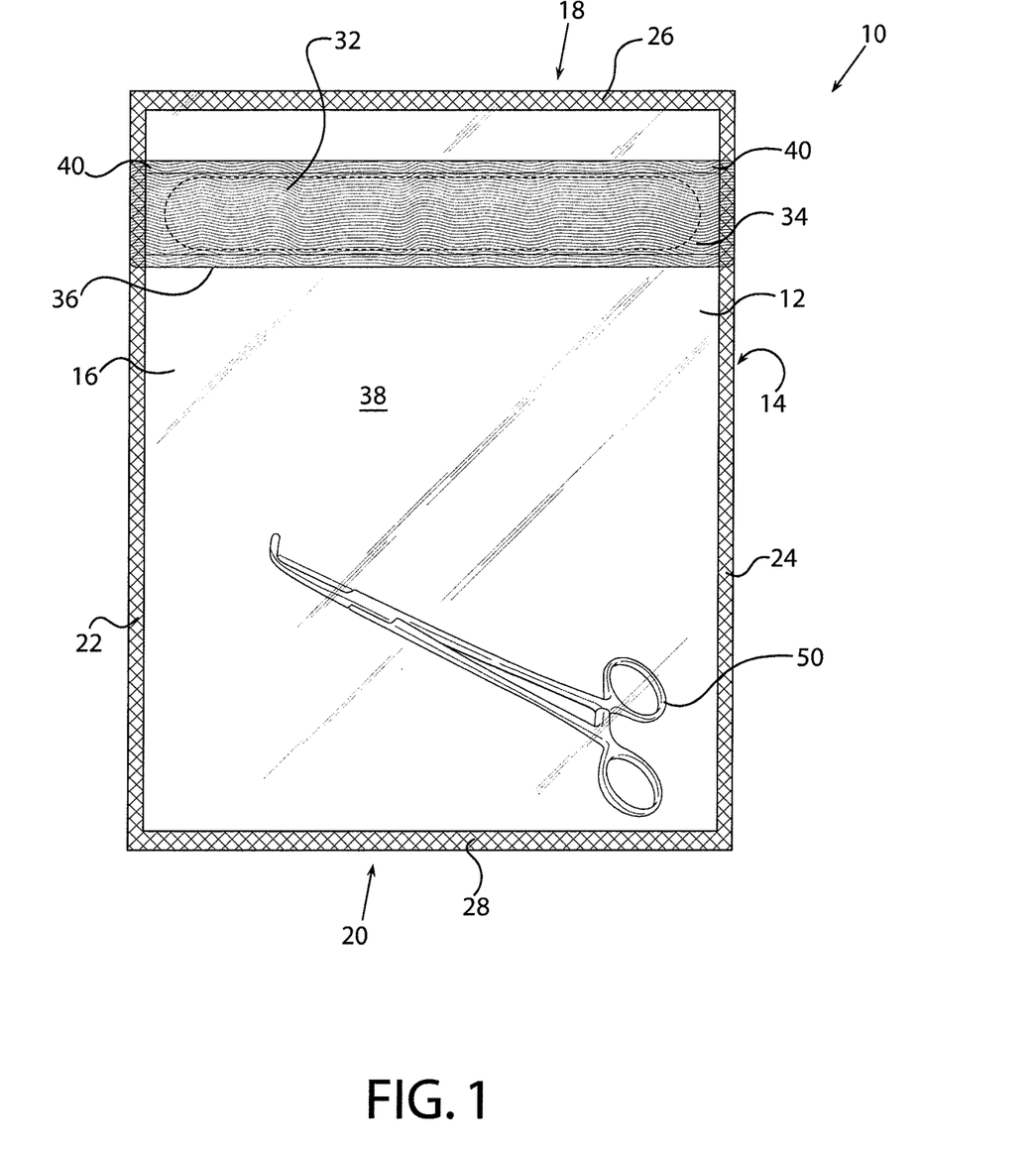
FIG. 1 is a plain view of a sterilizable pouch in accordance with one embodiment of the invention.
Figure 2:
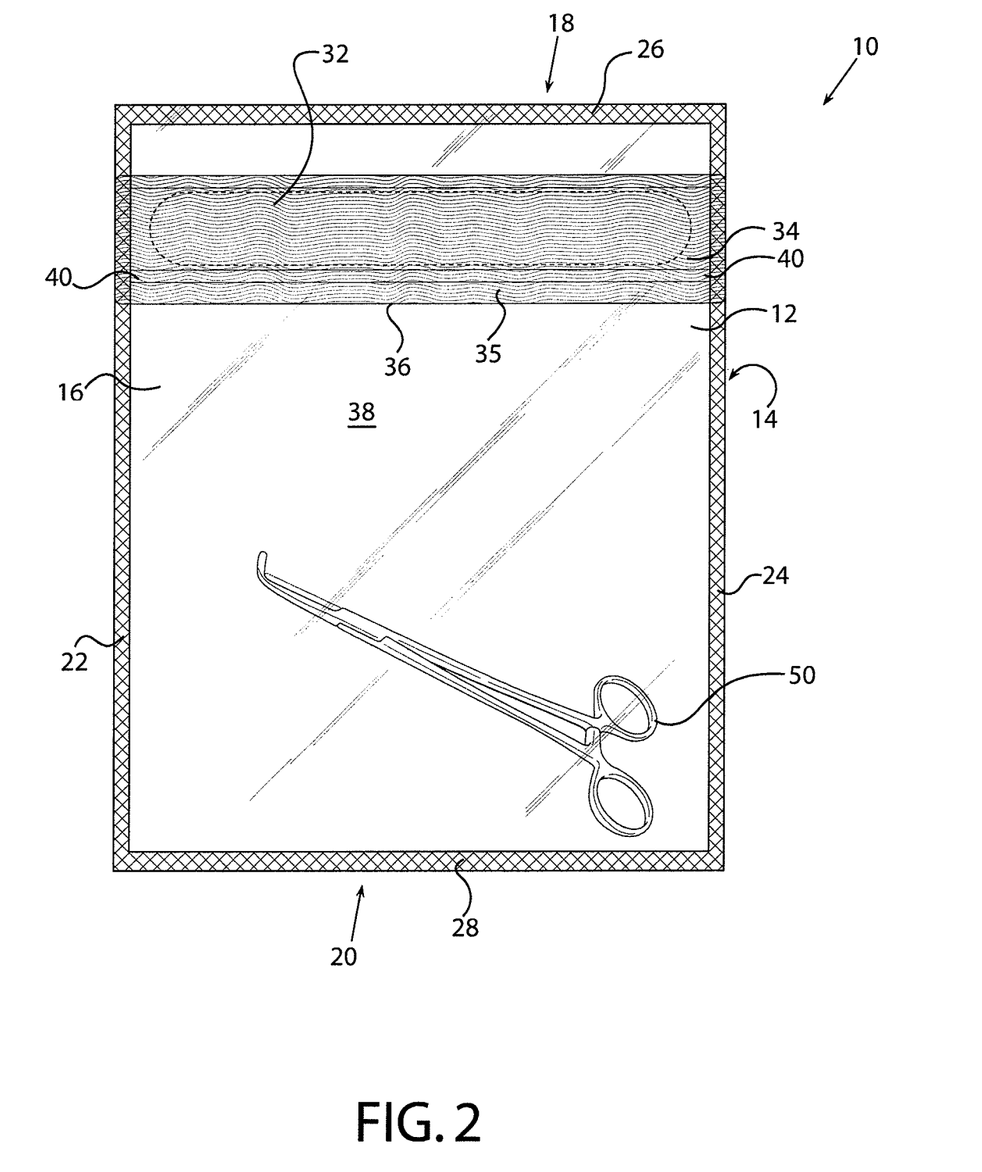
FIG. 2 is a plain view of a sterilizable pouch in accordance with an alternative embodiment of the invention.
Figure 3:
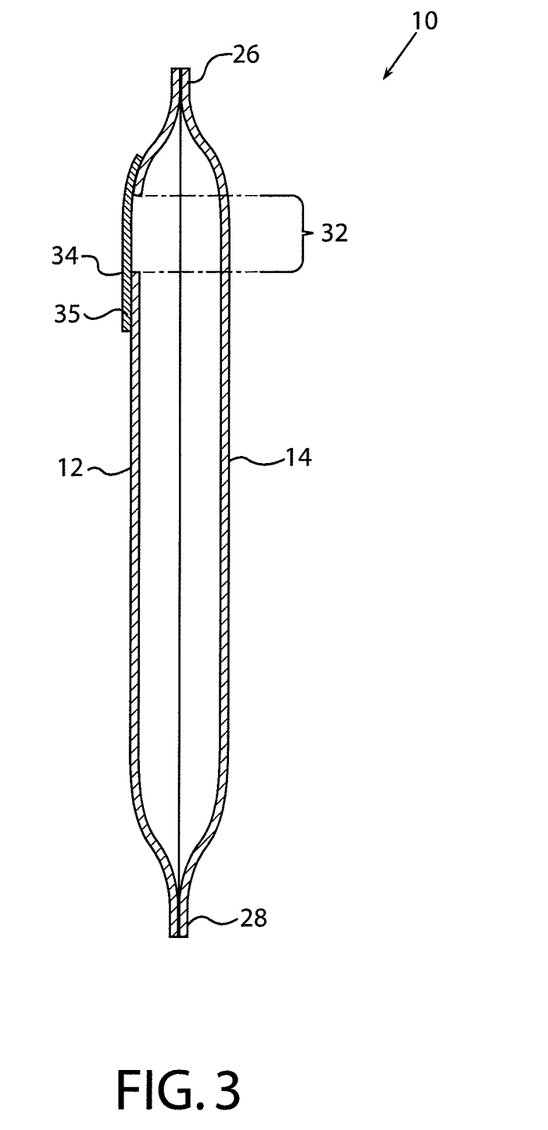
FIG. 3 is a cross section of the sterilizable pouch of FIG. 2.

With reference to FIGS. 1-3, sterilizable pouches that are in accordance with at least one embodiment of the present invention are illustrated and broadly designated by reference character 10. FIG. 3 is a side view of the pouch depicted in FIG. 2. The pouch 10 comprises front and back sheets 12, 14 that are arranged in opposing face-to-face relation with each other and are interconnected to define an interior space 16 of the pouch. The pouch includes a top end 18, a bottom end 20, and a pair of opposing side seams 22, 24 that extend longitudinally between the top and bottom ends of the pouch. In the illustrated embodiments, the top end of the pouch is sealed with top seam 26 and the bottom end of the bag is sealed with bottom seam 28. In the context of the invention, the term "pouch" is used in a generic sense and should be recognized to include, sacks, bags, satchels, packages, containers, and the like.

As described in greater detail below, the front and back sheets 12, 14 each individually comprise a flexible film comprised of a polymeric material having microbe barrier properties. In a preferred embodiment, the films comprising the front and back sheet each include liquid, moisture vapor, and gas barrier properties.

In the embodiment shown in FIGS. 1-3, the sterilizable pouch is shown in a sealed state with an article disposed in the interior space of the pouch. As discussed below, embodiments of the pouch can be prepared in which one of the ends of the pouch (e.g., the top or bottom end) is left open during manufacturing so as to provide an opening through which an article can be introduced into the pouch during the packaging process. The opening can then be sealed with a heat seal after an article has been inserted.

At least one of the front or back sheet includes an opening 32 formed therein and a breathable material 34 overlying and covering the opening. As discussed in greater detail below, the breathable material comprises a microbe barrier, gas permeable, material that permits a sterilizing gas to be introduced into the interior space of the pouch while preventing microorganisms from passing into the pouch. During sterilization, a sterilizing medium, such as a gas, is introduced through the breathable membrane and into the interior space of the pouch to sterilize an article 50 disposed therein.

In the illustrated embodiment, the opening 32 and the breathable material 34 are positioned towards a top portion of the front sheet 12. However, it should be recognized that the opening and breathable material can be positioned at other locations on the pouch including on the back sheet or towards a central or bottom portion of the front and back sheets. In addition, the pouch may include one or more such breathable openings as desired.

The breathable material 34 preferably comprises a sheet material that permits the passage of gases, including oxygen, carbon dioxide, and various sterilization gases, while limiting the passage of undesirable materials, such as microorganisms. Suitable materials for the breathable material may include nonwovens, medical grade paper, microbial barrier membranes, and other porous materials that limit the passage of microbes. Suitable nonwoven sheet materials include spunbond nonwoven fabrics, such as polypropylene and nonwoven fabrics formed of flash-spun polyethylene strands, such as a nonwoven sheet material sold by E.I. Du Pont de Nemours and Company under the trademark TYVEK®. In a preferred embodiment, the breathable material comprises an uncoated nonwoven fabric.

In one embodiment, the breathable material has a peripheral edge 36 and is joined to an outer surface 38 of front sheet 12 along a continuous seam 40 that is located towards or adjacent to the peripheral edge 36 of the breathable material 34. Preferably, the breathable material is joined to the sheet material with a heat seal. As shown in the illustrated embodiments, a portion of the breathable material 34, including a portion of the continuous seam 40, may overly opposing side seams 22, 24.

The film in which the opening 32 is formed (the front sheet 12 in the illustrated embodiment) comprises a multilayer polymeric material, such as a multilayer film, having a peel feature such that the breathable material can be peelably removed from the outer surface of the front or back sheet without tearing of the breathable material.

The inventors of the present invention have found that attaching the breathable material to a film having a peel feature may provide several advantages. One such advantage is that a peelable breathable material can be provided in the absence of having to use a coating on the breathable material in order to make the breathable material "peelable" from the surface of the front sheet. The presence of a coating on the breathable material can result in a substantial decrease in the porosity and breathability of the breathable material, which in turn may require longer cycle times during the sterilization time. By using an uncoated breathable material, the time required for sterilization can be significantly reduced.

In addition, the inventors have observed that the use of a film having peel feature layer may also help to reduce the amount of particulate matter (e.g., fibers and particles) that are created when removing the breathable material. In particular, it has been observed that pouches in accordance with the present invention may help to significantly reduce the amount of particulate matter released during removal of the breathable material from the surface of the pouch in comparison to pouches in which a coated breathable material (e.g., a coated TYVEK®) is heat sealed to the surface of the pouch. For example, in some embodiments it has been observed that removal of the breathable material by peeling the breathable material away from the film produces less than 10 particles, and preferably 8 or less particles having a particle size greater than 1 µm, and less than 15 particles having particles size ranging between 0.5 and 1 µm, and preferably 13 or less particles having particles size ranging between 0.5 and 1 µm, and less than 25 particles having particles size ranging between 0.3 and 0.5 µm, and preferably 21 or less particles having particles size ranging between 0.3 and 0.5 µm.

With reference to FIGS. 2-3, an embodiment of the sterilization pouch 10 is illustrated in which the breathable material 34 includes an unsealed region 35 that is disposed along a portion of the peripheral edge 36 of the breathable material 34. The unsealed region 35 provides a lip that is unattached to the surface of the breathable material so as to provide a surface that can be grasped and pulled when peelably removing the breathable material from the pouch. For example, at a time when it is desirable to remove the contents of the pouch, an individual can open the pouch by grasping the unsealed region with his/her fingers and then apply a peeling force to peel back and remove the breathable material.

In the illustrated embodiment, the unsealed region 35 is disposed towards the bottom end of the breathable material between the continuous seam 40 and the peripheral edge 36. However, it should be recognized that the unsealed region can be disposed at other locations along the peripheral edge 36 of the breathable material, such as, along the bottom or side ends of the breathable material. In one embodiment, the unsealed region 35 extends from about 0.5 to 15 cm beyond the continuous seam, and in particular, from about 0.5 to about 6, and more particularly, from about cm 0.75 to about 1.25 cm.

Figure 4:
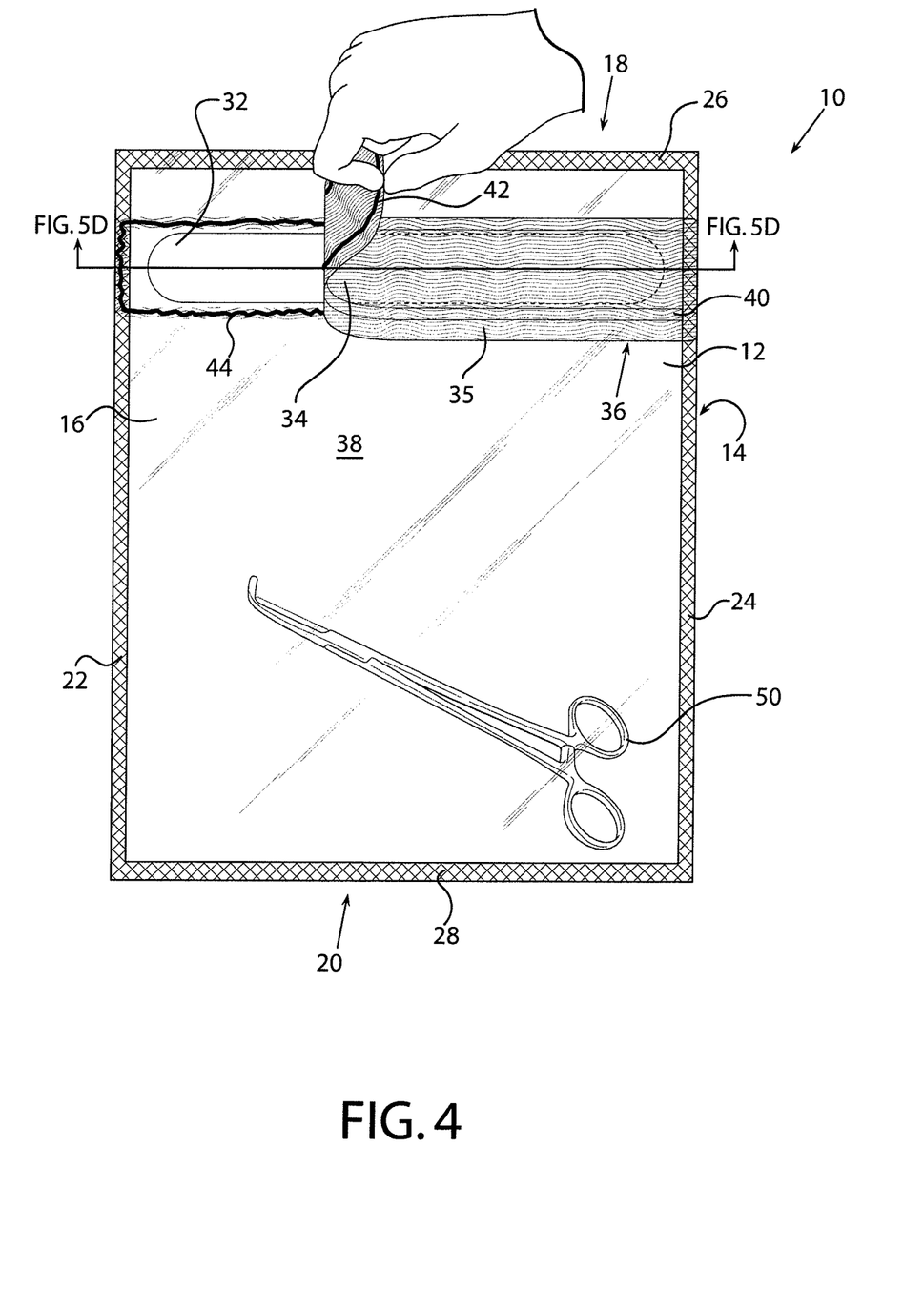
FIG. 4 shows a pouch in accordance with an embodiment of the present invention in which the breathable material is being peeled away to gain access to the opening of the pouch.

In one embodiment, the peal feature of the film comprises an intermediate rupture layer that is disposed in the interior of the film. For example, in one embodiment, the film includes an outer heat seal layer defining the outer surface of the film, and an intermediate rupturable layer (see, for example, FIG. 5A, reference character 54) underlying the heat seal layer. As discussed in greater detail below, the peel strength of the intermediate rupturable layer is less than the peel strength of the continuous seam 40 between the breathable material and the outer surface of the film. As can best be seen in FIG. 4, access to the opening 32 can be gained by peeling back the breathable material 34 which results in rupturing of the intermediate rupturable layer along the continuous seam. FIG. 4 further shows remnants of a portion of the continuous seam may be present on an inner surface of the breathable material (identified by reference number 42), and a rupture of the sheet material coinciding with the previous position of the continuous seam (identified by reference number 44).

In embodiments in which the peel feature comprises an intermediate rupturable layer, it is believed that the heat sealing process between the breathable material and the outer surface of the film may help reduce the production of particular matter that is produced when the breathable material is peeled away. In this regard, FIGS. 5A-5D illustrate a cross-section of the seal between the breathable material and the film as the breathable material is peeled away from the film. In the illustrated embodiment, the film 30 is shown as a multilayer film having four distinct layers in which the film includes an outer layer 52 which defines an outer surface of the pouch, an intermediate rupturable layer 54 disposed adjacent to the outer layer 52, an interior core layer 56, and an outer heat seal layer 58. As discussed below, outer heat seal layer 58 generally defines an inner surface of the front and back sheets that is capable of being heat sealed to itself or another film structure to define the sterilizable pouch.

It should be recognized that the number of layers can be varied. For example, the sheet material may have 2 or more layers, 4 or more layer, 5 or more layers, 6 or more layers, 7 or more layers, 8 or more layers, and 10 or more layers.

Figure 5A:
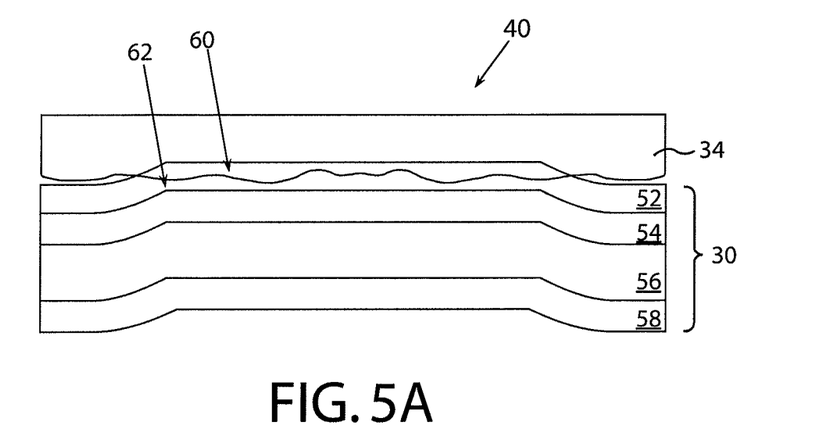
FIGS. 5A-5D are cross-sections of the continuous seam between the breathable material and a sheet material having an intermediate rupturable layer.

As shown in FIG. 5A, the breathable material 34 is adhered to the outer layer 52 of the film 30 with a heat seal to form continuous seam 40. During the sealing process, a portion of the outer layer 52 may become molten and flow into the breathable material at the interface 60 of the breathable material 34 and the outer layer 52. It is believed this may also lead to a partial thinning of the thickness of the outer layer 52 along the continuous seam 40 between the interface 60 and the intermediate rupturable layer 54 (see, for example, reference character 62).

Figure 5B:
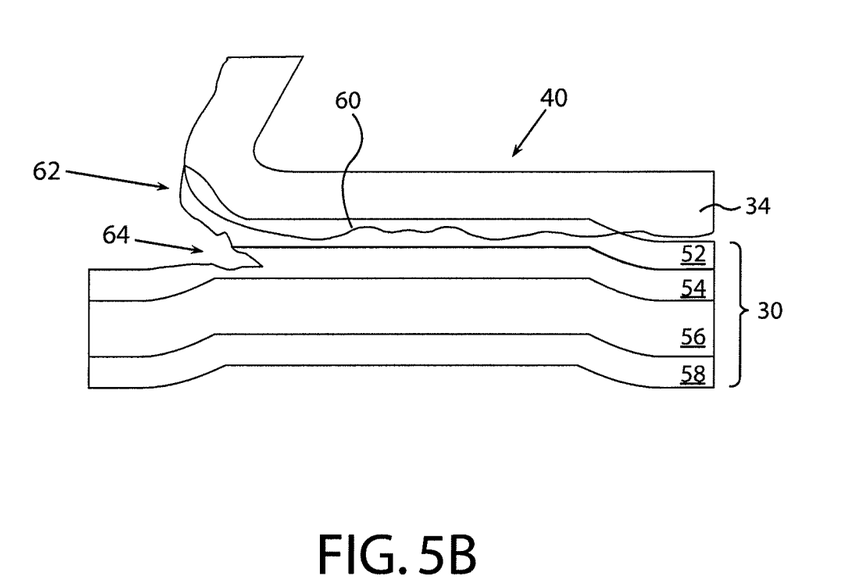
Figure 5C:
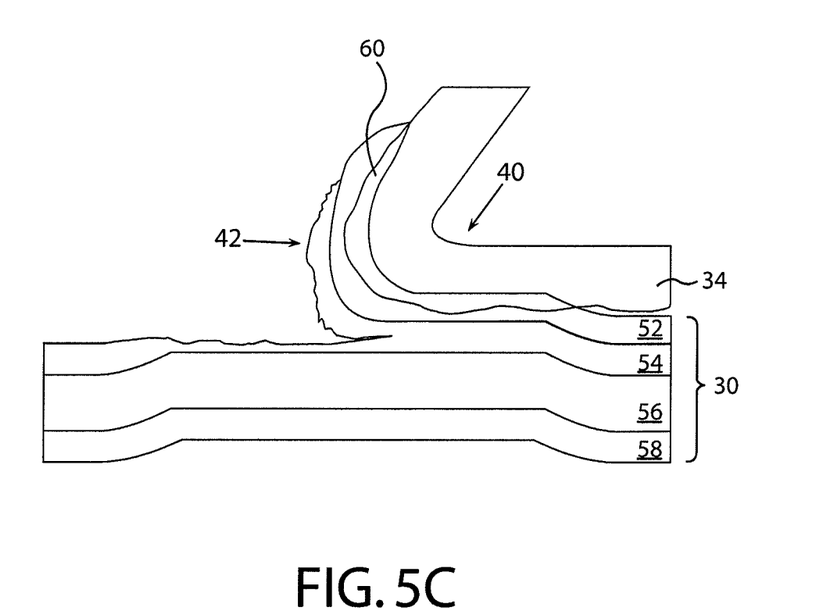
Figure 5D:
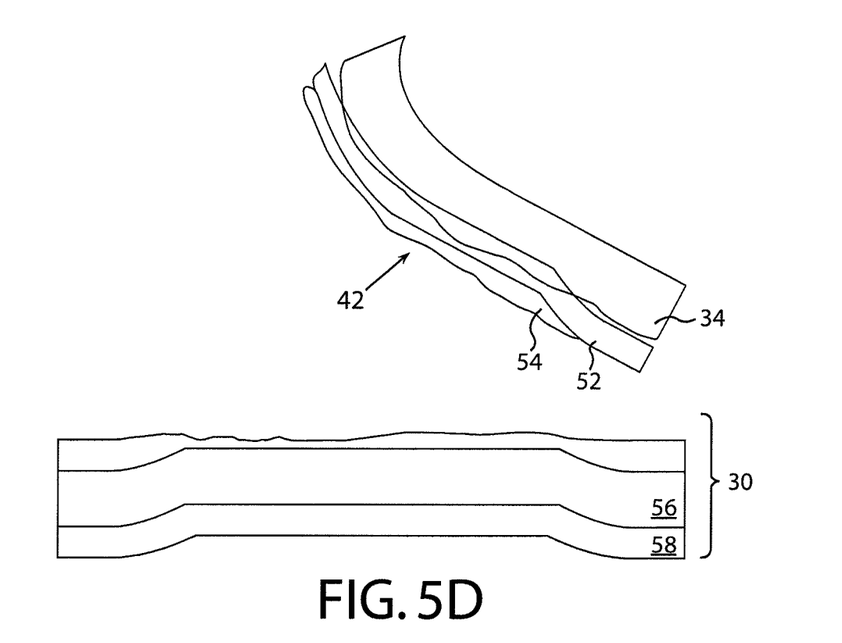

As can best be seen in FIGS. 5B-5C, the peeling away of the breathable material from the film 30 results in forming a tear 64 of the outer layer 52 at the interface 60. Continuing to apply a peeling force to the breathable material causes the intermediate rupturable layer 54 to cohesively rupture internally and thereby propagate the tear along the continuous seam. As shown in FIGS. 5C and 5D, continued peeling of the breathable membrane results in propagation of the tear in intermediate rupturable layer 54 so that the continuous seam 40 is destroyed and the breathable material can be partially or fully removed from the pouch. As shown in FIG. 5D, a portion 42 of the film 30 may remain attached to the breathable material.

The outer layer 52 generally comprises a material that is heat sealable to the breathable material. Preferably, the outer layer is capable of forming a heat seal to the breathable material 34. The polymer forming the heat seal layer should be such that at the temperatures used to form heat seals, for example 110 to 180° C., it should have a sufficiently low viscosity that it penetrates into and around the fibers of the breathable material to which the film is being heat sealed. Penetration of the outer layer into the breathable material in general serves to effect a mechanical interlocking between the outer layer and the breathable material. The depth of penetration and the degree of interlocking generally depends upon the chemical composition and the relative quantities of the materials forming the outer layer, the fiber dimensions, packing and type, the openness of the sealing face of the breathable material, and the heat sealing temperature, pressure and dwell time.

In addition, in embodiments in which the peel feature comprises an intermediate rupturable layer, it may be desirable that the outer layer is sufficiently brittle to facilitate rupture through to the intermediate rupturable layer where peeling takes place. For example, the outer layer may include a brittle additive that helps facilitate tearing of the outer layer when the breathable material is peelably removed from the pouch. In one such embodiment, the outer seal layer may comprise a polyolefin that is blended with a polymer which is itself a brittle solid at room temperature but which has a low viscosity when melted. Examples of polyolefins which can be used to form the heat seal layer include polyethylene, for example low density polyethylene or linear low density polyethylene, and copolymers of propylene and ethylene. The brittle additive is preferably compatible with the polymer with which it is blended, and examples of such additives include poly-di-pentene, polyterpenes, α-methyl styrene resins, vinyltoluene/α-methyl styrene resins, modified aromatic resins and other low molecular weight hydrocarbon resins. Examples of brittle additives which can be used in accordance with the present invention may include hydrogenated and pure monomer hydrocarbon resins.

The relative amounts of polymer and brittle additive in the outer layer can usually be varied widely. However, very small amounts of a brittle additive will result in the outer layer itself being insufficiently brittle to break upon peeling when the heat seals are peeled, and very large amounts of such an additive can adversely affect the heat seal and other properties of this layer. Preferred blends contain at least 5 wt % of a brittle additive, but it is generally preferred that they should contain no more than 30 wt % of such an additive.

In embodiments in which the peel feature comprises an intermediate rupturable layer, the heat seal between the breathable material and outer layer (e.g., the continuous seam 40) typically has a seal strength that is greater than the cohesive strength of the intermediate rupturable layer. In other words, the intermediate rupturable layer has a peel strength that is less than the peel strength of the heat seal joining the breathable material to an outer surface of the pouch.

In some embodiments, the outer layer 52 may also include heat resistant properties. In one embodiment, the outer layer has heat resistant properties that are less than the heat resistance of the outer heat seal layer 58. As discussed in greater detail below, such a structure is contrary to typical conventional heat sealing techniques for converting films into pouches. In one embodiment, outer layer 52 has a melting point that is from 100 to 114° C. less than the melting point temperature of the outer heat seal layer 58, and in particular, from 128 to 135° C. less than the melting point temperature of the outer heat seal layer 58. Suitable polymers for the outer layer may include one or more of any of the following: polyolefins (e.g., polyethylenes, polypropylenes), polyamides, polyesters, and polystyrenes. Examples of suitable polyesters include amorphous (co)polyesters, poly(ethylene/terephthalic acid), and poly(ethylene/naphthalate). In a preferred embodiment, the front and back sheets include an outer layer 52 comprising polyethylene.

The intermediate rupturable layer comprises a material having sufficient interior cohesive strength so that pouch can be exposed to typical processing and handling conditions without rupture of the intermediate rupturable material. The intermediate rupturable layer serves to impart peelability to film by cohesive splitting within the thickness of this layer. However, it may be desirable that the force per unit area required to effect peeling of the seal is less than the force per unit area required to remove fibers from a fibrous material when the film has been heat sealed to such a material.

A wide variety of different materials may be used for the intermediate rupturable layer provided that the materials have sufficient coherent strength to withstand the packaging and sterilization process and also conditions typically encountered during transport to the end user. For example, in one embodiment the intermediate rupturable layer may comprise a blend of incompatible polymers such that the internal cohesiveness of the layer is weakened or reduced. Alternatively, the intermediate rupturable layer can comprise a blend of one or more polymers and filler. For example, the intermediate rupturable layer may comprise a blend of a polyolefin with organic or inorganic fillers. Examples of polyolefins which can be used to form the intermediate layer include polyethylenes, for example low density polyethylene, and copolymers of propylene and ethylene. Low density polyethylene and polypropylene are particularly preferred as they have a low elongation at break when compared with other polyolefins, for example polybut-1-ene and linear low density polyethylene.

Any of a wide variety of fillers can be used to impart cohesive splitting to the intermediate rupturable layer, such fillers serving to reduce the internal cohesive strength of the polymer used to form the layer. The filler can be organic or inorganic, examples of fillers which can be used for the purpose including chalk, talc, titanium dioxide, barium sulfate, magnesium sulfate, polybutene, polypropylene and other incompatible polymers. In addition, the term filler can include a gas which can be introduced using a foaming agent blended into the intermediate layer which foams the intermediate layer at the elevated temperatures to which the polymer melt is subjected during any hot extrusion process. Foaming can also reduce the internal cohesive strength of the polymer used to foam the layer.

The amount of filler required to reduce the cohesive strength of the intermediate rupturable layer so that it will peel by splitting within its thickness can be varied within wide limits. However, if insufficient filler is present, the force required to effect peeling can become excessive, and if very large amount of filler are used, the intermediate layer can become too weak. In some embodiments, the intermediate rupturable layer may contain from 15 to 65 wt % of filler, and more particularly from 45 to 55 wt %. As will be appreciated, particulate fillers in the intermediate rupturable layer may impart at least some degree of opacity to the films, and it may be possible to reduce this opacity by the inclusion of an incompatible polymer in this layer. For example, the addition of polybutylene to polyethylene can enable lower amounts of inorganic filler to be used to achieve substantially the same peel strength. More particularly, substantially similar peel strengths can be achieved, but with reduced opacity, by using a blend of 55 wt % of low density polyethylene and 15 wt % of polybutylene containing 30 wt % of talc rather than a 50:50 (wt/wt) mixture of low density polyethylene and talc.

Changing the polymer of the intermediate rupturable layer may necessitate the use of different incompatible polymers in the intermediate rupturable layer. For example, if propylene based copolymers with ethylene are used as the base polymer for the intermediate layer, other polymers can be used to reduce the amount of inorganic filler required to reduce the cohesive strength of the intermediate layer, e.g. ethylene based ionomers and low density polyethylene.

In one embodiment, the intermediate rupturable layer is selected so that the resulting peel strength of the breathable material from the film is less than about 4 lb./in. as measured by ASTM test F88. In one embodiment, the peel strength of the breathable material to the film is from about 0.75 lb./in. to 3.5 lb/in., and more typically from about 1 to 2 lbs./in., and even more typically from about 1 to 1.75 lbs./in In alternative embodiments, the peel feature of the film may be provided by the outer layer 52 of the film. In this embodiment, the outer layer may comprise a blend of polymeric materials that result in the interface of the continuous heat seal to the film being subject to cohesive failure when a peeling force is applied. For example, the outer layer may include a blend of polymeric components which result in a reduction of the peel strength of the breathable material to the film. For instance, the outer layer may comprise a blend of a polyethylene or polyamide, and a contaminant, such as polybutylene. In this embodiment, the peel strength between the breathable material and the outer layer of the film is less than about 4 lb./in. as measured by ASTM test F88.

Figure 6A:
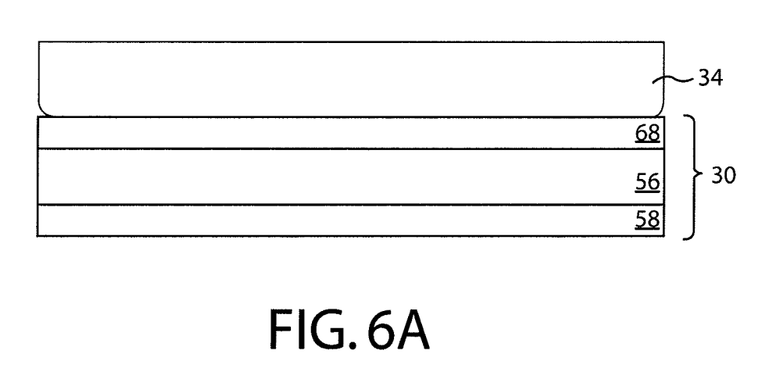
FIGS. 6A and 6B are cross-section of an alternative embodiment of the invention in the process of having the breathable material peeled away from the surface of the pouch.
Figure 6B:
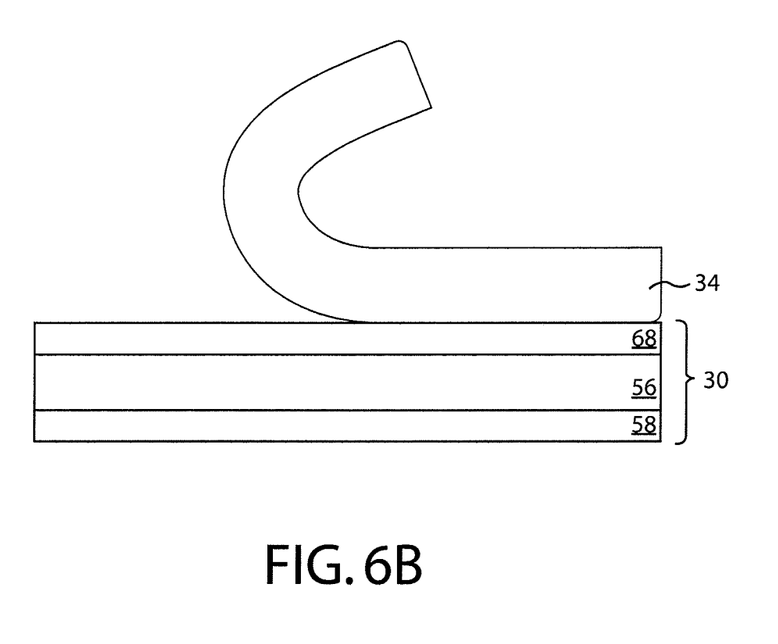

In this regard, FIGS. 6A and 6B illustrate an embodiment of the invention in which the outer layer 68 of the film 30 includes a peel feature so that the breathable material can be peeled away from the surface of the film. In FIG. 6B, the breathable material is depicted in the process of being peelably removed.

Polymeric films suitable for use as a film in pouch may include one or more additional layers that impart desired properties to the film. For example, the film may include one or more functional layers, bulk layers, tie layers, and the like. For example, the film may include one or more interior core layers (see, for example, reference character 56 in FIGS. 5A and 6A). In one embodiment, the interior core layer may be composed of compositions selected to impart specific properties to the film, such as barrier properties. Suitable components the film may include metallic foil, such as aluminum foil, and metallized films, such aluminized films, aluminum oxide films (AlOx), silicon oxide films (SiOx), and films comprising polychlorotrifluoroethylene (PCTFE) such as ACLAR®. The film may also include polymeric components having barrier properties, such as ethylene/vinyl alcohol copolymer ("EVOH"), vinylidene chloride polymers ("PVdC"), polyalkylene carbonate, polyester (e.g., PET, PEN), polyacrylonitrile ("PAN"), and polyamides.

Useful polyamides may include polyamide 6, polyamide 9, polyamide 10, polyamide 11, polyamide 12, polyamide 66, polyamide 610, polyamide 612, polyamide 61, polyamide 6T, polyamide 69, copolymers made from any of the monomers used to make two or more of the foregoing homopolymers (e.g., copolyamide 6/12, polyamide 12, copolyamide 66/69/61, copolyamide 66/610, copolyamide 6/66, and copolyamide 6/69), and blends of any of the foregoing homo- and/or copolymers.

The film may also include a sealant layer on the opposite side of the film from the heat sealable outer layer (see, for example, outer heat seal layer 58 in FIGS. 5A and 6A). The sealant layer typically defines an inner surface of the sterilizable pouch that faces the interior space of the pouch. The polymer material (i.e., component or blend of components) that forms the sealant layer has a melting point that facilitates heat sealing the inner surface of the sheet material to a second sheet material, such as in the embodiment illustrated in FIG. 1, or to itself. Useful material for this sealant layer may include the ones mentioned above in connection with the outer layer.

Sterilizable pouches in accordance with the present invention can be used to package a variety of different articles including medical instruments and devices. For example, the sterilizable pouch can be used to package and sterilize, scalpels, scissors, sutures, forceps, retractors, blades, clamps, stents, both treated and untreated, catheters, surgical drapes and gowns, surgical and procedural kits, etc.

Sterilizable pouches in accordance with the present invention can be prepared using methods commonly used in forming pouches/bags. For example, in one embodiment pouches in accordance with the present invention can be prepared by separately providing two distinct film sheets of material that are to define the front and back sheets. Generally, the film sheets are provided via a roll stock material from which each sheet material is unwound. At least one of the sheet materials includes a cut-out or hole which will form the opening of the breathable material (see reference number 32 in FIG. 1). The opening can be formed in the film prior to being wound onto the roll stock or, alternatively, can be formed in the sheet material just prior to forming the pouch. The opening 32 can be made in the film comprising the front or back sheets in a variety ways as known in the art, including punching, die cutting, cutting, and the like.

The film in which the opening is to be formed will include an intermediate rupturable layer as discussed above. In one embodiment, the films defining the front and back sheets are the same, and in other embodiments, the back sheet may have a different structure and/or composition from that of the front sheet.

Referring back to FIG. 1, the breathable membrane in the front or back sheet can be formed by heat sealing the breathable material to the outer surface of the film to form continuous seam 40. As in the opening in the film, the breathable material can sealed to the film prior to being wound onto the roll stock or, alternatively, can be formed in the sheet material just prior to forming the pouch.

In one embodiment the films defining the front and back sheets 12, 14 are superimposed opposite to each other and are then joined to each other along the opposed side seams 22, 24. The side seams, as well as the other seams of the pouch to be described presently, can be formed by any of various methods conventionally used in the packaging industry provided the seams are substantially impervious to the ingress/egress of liquids and gases. Preferably, the various seams are substantially impervious to gases such as moisture vapor, oxygen, carbon dioxide, etc. Suitable methods for forming the seams may include adhesive or fusion bonding, such as by forming seals with heat or ultrasonic energy. In the particular embodiment illustrated, the front and back sheets are made from a heat sealable material and the various seams are formed by producing a fusion bond or seal between contacting interior surfaces of the front and back sheets using pressure and heat or ultrasonic energy as is well known. Although referred to herein as "heat seals", it should be understood that this term is intended to apply both to seals formed by heating the contacting surfaces with a heated anvil or platen, as well as to heating and fusion produced by other methods, such as application of ultrasonic energy.

During manufacturing of the pouch, one of the ends of the pouch (e.g., the top end 18 or the bottom end 20) is typically open so that an opening is provided for introducing an article into the interior space of the pouch. Once an article is introduced into the pouch, a heat seal can be used to bond the inner surfaces of the front and back sheets to each other and thereby form top seam 26 or bottom seam 28.

Alternatively, a pouch can be prepared from a single sheet of film in which the film is center folded to form a c-fold in the film, which in turn defines the front and back sheets disposed opposite each other.

Figure 8:
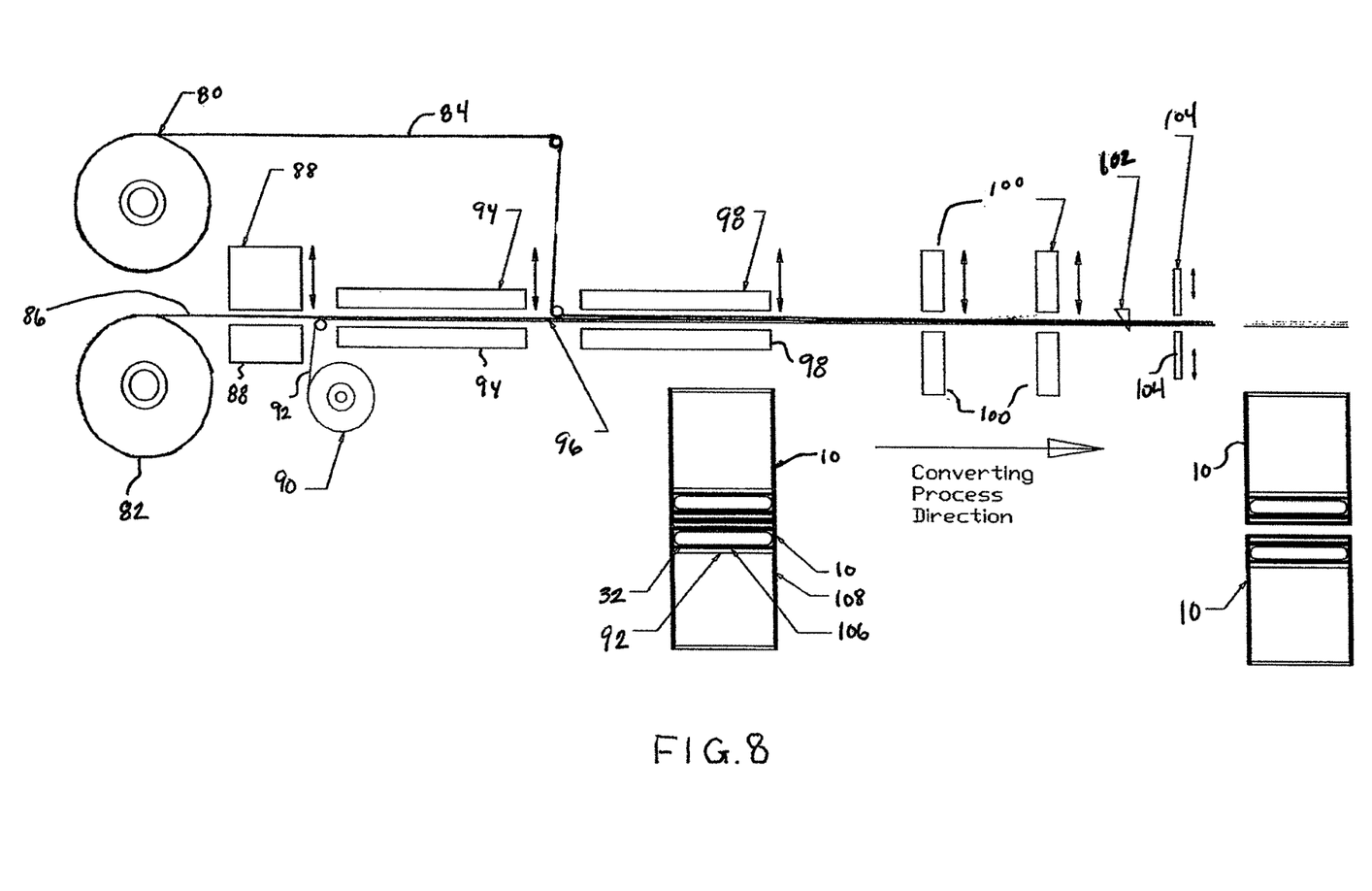
FIG. 8 is a schematic illustration of a system that may be used to produce sterilizable pouches in accordance with embodiments of the present invention.

With reference to FIG. 8, an exemplary system and method of preparing a sterilizable pouch in accordance with at least one embodiment of the invention is illustrated. As shown, the system includes first and second supply rolls 80, 82, respectively, for providing films from which the sterilizable pouch is manufactured. Supply roll 80 provides a first film 84, which will be used to prepare the back sheet of the pouch, and supply roll 82 provides a second film 86, which will be used to prepare the front sheet.

A cutting device 88 is positioned downstream of supply roll 82 for forming an access opening see reference number 32 in FIG. 1) in the second film (i.e., the front sheet). As noted previously, the opening can be made in a variety ways as known in the art, including punching, die cutting, cutting, and the like. A sheet of breathable material 92 is supplied via supply roll 90 and is sealed to the outer surface of second film 86 via sealing device 94 such that it overlies the previously formed opening. Sealing device 94 includes a pair of opposing seal elements that are configured to apply pressure and heat to the breathable material and second film.

In contrast to conventional heat sealing techniques, the present inventors have discovered that to improve the formation of a peelable seal between the breathable material and an outer surface of the second film, it may be desirable to use a film structure in which the outer layer of the film (e.g., layer 52 of FIG. 5A) has a lower melting threshold than the layer of the film forming the outer heat seal layer (e.g., layer 58 of FIG. 5A) of the pouch. In conventional package conversion processes, the outer layer of the film defining the exterior surface of the pouch generally has a higher temperature threshold than the layer being heat sealed to other film. The reason for this conventional structure is because the outer layer (e.g., layer 52) may be directly exposed to a heat seal bar, or similar sealing device, of the heat-sealing equipment when sealing the front and back sheets to each other to form the pouch to help prevent "burn-through" and sticking during heat sealing.

In embodiments of the present invention, it has been found that improved peelability of the breathable material from the pouch may be provided by selecting a resin for the outer layer of the second film 86 having lower heat resistance than the layer of the film that is to be heated sealed to first film 84. However, in some embodiments, it has been observed that the use of an outer layer of the film having a lower melting threshold may result in processing difficulties because of adhesion of the film to a sealing device. In this regard, the inventors have discovered that rapid heat sealing followed by rapid quenching of the seal may help alleviate this problem.

In one embodiment, it has been found that improved seals at sealing device 94 can be prepared by quickly heat sealing the breathable material to the second film followed by immediately quenching the sealing area while the film and breathable material is still under pressure between the sealing elements. In one embodiment, this rapid quenching may be accomplished by introducing a cooling fluid, such as water, in or around the sealing elements of the sealing device immediately after the seal is formed. For example, in one embodiment, the heat seal between the breathable material and the second film may be formed by exposing the film and breathable material to heat and pressure for about 100 to 500 milliseconds (ms), and in particular from about 250 to 350 ms, followed by immediately quenching and cooling of the sealing elements for about 500 to 900 ms, and in particular, from about 650 to 750 ms.

After the seal has been quenched, the sealing bars are released and the second film is driven forward and first film is positioned so that it overlies the second film at 96. The first and second films are then driven forward until a second sealing device 98 creates longitudinal seams 106 to join the first and second films to each other. Following sealing device 98, sealing devices 100 are used to create cross-direction seams 108 between the first and second films.

As discussed previously in connection with heat sealing device 94, the longitudinal and cross-direction seams are created by quickly heat sealing the first and second films to each between a pair of opposing heating elements under pressure, and that is followed by immediately quenching the heat seal while the first and second films are still under pressure between the sealing elements.

The conversion process can then be completed by cutting devices 102 and 104 that are positioned downstream of sealing device 100. In the embodiment illustrated in FIG. 8, the system and associated process are used to concurrently prepare a pair of sterilizable pouches in a side-by-side configuration. Cutting device 102 is then used to separate the two pouches from each other with a machine direction cut.

EXAMPLES

In the following Examples, the generation of particulate matter upon removal of the breathable material from the film was explored.

In Comparative Example 1 a film comprising an outer layer of polyethylene terephthalate (PET) and a base layer of polyethylene (PE) was heat sealed to a breathable material of coated TYVEK®.

In Comparative Example 2 a film comprising an outer layer of polyethylene terephthalate (PET) and base layer of polyethylene (PE) was heat sealed to a breathable material of uncoated TYVEK®.

In Example 1, a three layer film having an outer heat seal layer comprising a polyethylene, an intermediate rupturable layer, and a base polyester layer was heat sealed to a breathable to a breathable material of uncoated TYVEK®.

The heat seal conditions in Comparative Examples 1-2 and Example 1 were selected to provide the optimum heat seal conditions. Following heat sealing, the breathable material was removed by hand peeling the breathable material away from the film. The amount of particulate matter generated during the peeling process was then evaluated by peeling the breathable material while the pouch was near an air sampling probe (peeling open the pouch 2-3 inches from the probe) and counting the number of particles released during the opening process, using an airborne particle counter in a clean environment.

Figure 7:
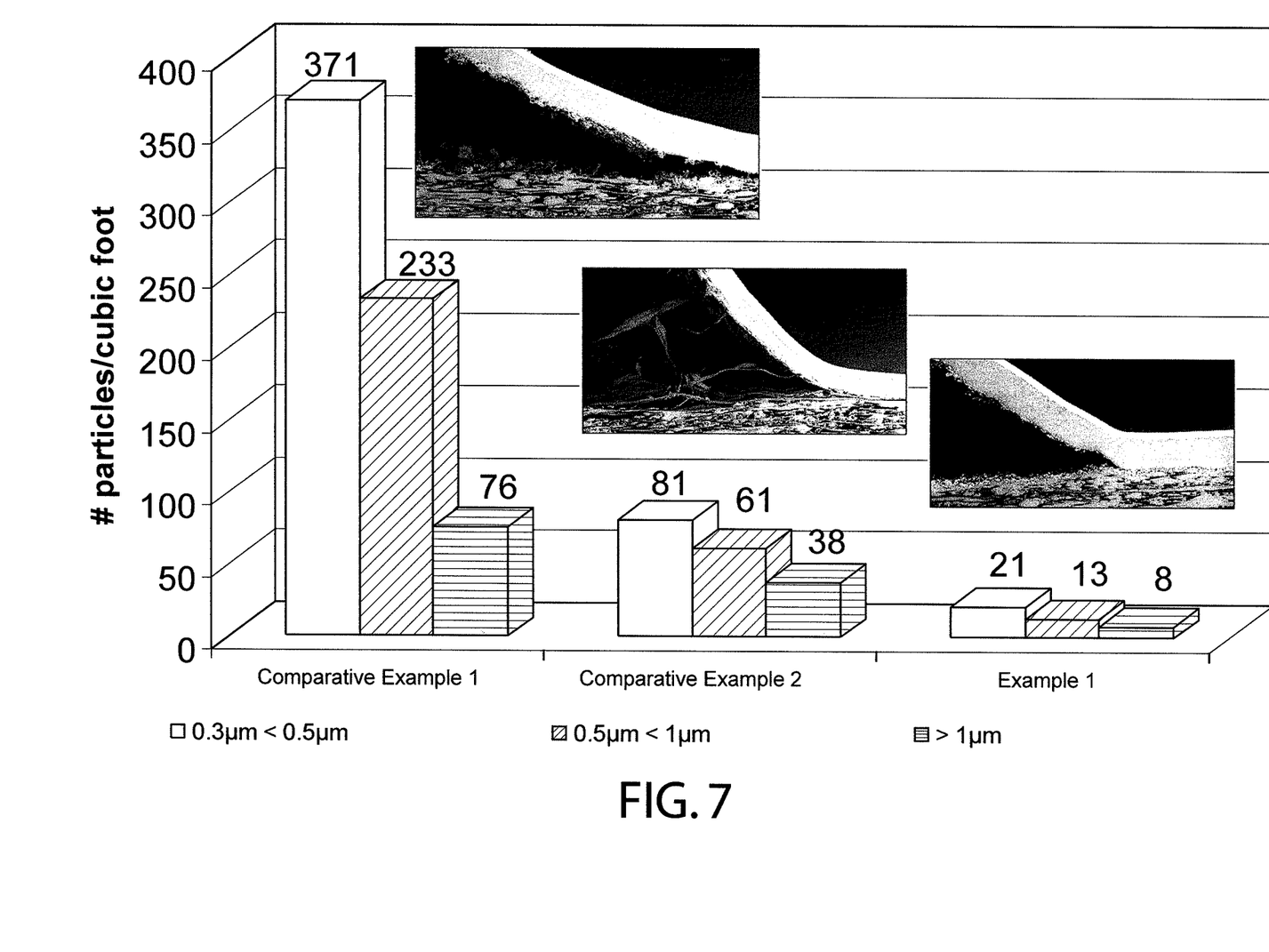
FIG. 7 is a graph with micrograph images that compares the amount of particles released upon removal of the breathable material.

The results of the tests are shown in the chart in FIG. 7 along with side micrograph images of the film showing the partial removal of the breathable material. The micrograph images were obtained with a digital microscope. As can be seen in FIG. 7, both Comparative Examples 1 and 2 produced a significantly greater amount of particles than Example 1. In particular, the films of Comparative Examples 1 and 2 resulted in a significantly greater amount of particles being produced across the three distribution ranges evaluated. Thus, it can be seen that pouches prepared in accordance with embodiments of the present invention can be used to produce pouches with breathable, peelable openings that can help significantly reduce air borne particles and larger particles upon removal of the breathable material.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A sterilizable pouch comprising:
   front and back sheets, each of a flexible, continuous film joined to each other along opposite side and bottom edges to define a pouch having an interior space for receiving an article therein, said film of said front sheet comprising a multilayer film having a first outer layer defining an outer surface of said front sheet and the pouch, and a second outer heat seal layer defining an inner surface of the front sheet and the pouch that is heat sealed to an opposing surface of the back sheet along the opposite side and bottom edges;
   an opening formed in said front sheet and being spaced apart from said opposite side and bottom edges, the opening for providing communication between an exterior environment of the pouch and said interior space;
   a breathable material overlying and covering said opening, and being joined to said outer surface of said front sheet with a continuous heat seal, said breathable material comprising an uncoated fibrous material that is impervious to microorganisms, but pervious to gases;
   wherein said multilayer film of said front sheet includes a layer having a peel feature such that the breathable material can be peelably removed from said outer surface of said front sheet without tearing of the breathable material; and
   wherein the first outer layer has a lower melting threshold than the second outer heat seal layer.

2. The sterilizable pouch according to claim 1, wherein said peel feature comprises the first outer layer of said multilayer film that is comprised of a blend of polymeric materials that are selected so that a peel strength of the continuous heat seal is less than 4 lbs./in.

3. The sterilizable pouch according to claim 1, wherein the peel feature of said multilayer film comprises an intermediate rupturable layer having a peel strength that is less than a peel strength of the continuous heat seal joining the breathable material to said outer surface, such that the breathable material can be removed by peeling the breathable material away from the outer surface of said front sheet which causes the intermediate rupturable layer to rupture along said continuous heat seal.

4. The sterilizable pouch according to claim 1, wherein the opposite side edges of the front and back sheets are joined to each other with the heat seal defining side seams of the pouch, and wherein the continuous heat seal joining the breathable material to said outer surface of said front sheet at least partially overlies said side seams.

5. The sterilizable pouch according to claim 1, wherein the breathable material includes a lip that is unconnected to said outer surface of said front sheet and that extends between the continuous heat seal and a peripheral edge of the breathable material.

6. The sterilizable pouch according to claim 5, wherein said lip extends between the continuous heat seal and the peripheral edge from about 0.5 to about 15 cm.

7. The sterilizable pouch according to claim 1, wherein the front and back sheets each include opposing top edges that are unconnected to each other to define an access opening into the interior space of the pouch.

8. The sterilizable pouch according to claim 1, wherein said opening is a cut-out that is created in the continuous film of the front sheet.

9. The sterilizable pouch according to claim 1, wherein the front sheet includes a continuous edge defining said opening.

10. The sterilizable pouch according to claim 1, wherein the opening is formed by cutting, punching, or die-cutting the front sheet.

11. The sterilizable pouch according to claim 1, wherein said opening provides direct access to the interior space of the pouch.

12. The sterilizable pouch according to claim 1, wherein there are no film structures disposed between the opening and the interior space of the pouch.

13. A sterilizable package comprising:
a sealed container having at least one wall formed of a flexible film, the at least one wall including a cut out defining an opening formed therein for providing communication between an exterior environment of the package and an interior space of the package;
a breathable material disposed on an outer surface of said at least one wall and covering said opening, and being joined to the at least one wall with a continuous heat seal, the breathable material being impervious to microorganisms, but pervious to gases,
wherein the flexible film forming said at least one wall comprises a multilayer film having a first outer layer defining said outer surface of the package to which the breathable material is joined via said continuous heat seal, a second outer heat seal layer defining an inner surface of the package that is heat sealed to an opposing film surface, and an intermediate rupturable layer having a peel strength that is less than a peel strength of the continuous heat seal joining the breathable material to said outer surface, such that the breathable material can be removed by peeling the breathable material away from the at least one wall which causes the intermediate rupturable layer to rupture along said continuous heat seal, and
wherein the first outer layer has a lower melting threshold than the second outer heat seal layer.

14. The package of claim 13, wherein the breathable material comprises uncoated paper or an uncoated nonwoven fabric.

15. The package of claim 13, wherein the package comprises front and back sheets that are sealed to each other along opposing adjacent edges to define said interior space, wherein said front sheet or said back sheet is defined by the at least one wall.

16. The package of claim 13, wherein the intermediate rupturable layer has a peel strength that is from about 0.75 to 3.5 lbs./in.

17. A sterilizable pouch comprising:
front and back sheets of a flexible film arranged in opposing face-to-face relation, each having an inner surface comprising a heat sealable thermoplastic material, a top edge, a bottom edge, and opposite side edges extending longitudinally from said top edge to said bottom edge, wherein the front sheet comprises a multilayer film having an outer layer, an outer heat seal layer defining the inner surface of the front sheet, and an intermediate rupturable layer;
side seams extending longitudinally along said opposite side edges and joining the front and back sheets to each other;
a bottom seam extending transversely along said bottom edges and joining the front and back sheets to each other;
an opening formed in the front sheet and providing communication between an exterior environment of the pouch and an interior space of the pouch, the opening being positioned directly opposite the inner surface of the back sheet;
a breathable material disposed on the front sheet and covering said opening, said breathable material comprising a moisture vapor permeable, water-impermeable sheet material;
a continuous seam located at or adjacent a peripheral edge of the breathable material joining the breathable material to the outer layer of the front sheet,
wherein a peel strength of the continuous seam is greater than a peel strength of the intermediate rupturable layer such that access to the opening can be achieved by peeling the breathable material away from the front sheet which causes the intermediate rupturable layer to rupture, and
wherein the outer layer has a lower melting threshold than the outer heat seal layer.

18. The pouch of claim 17, wherein the breathable material comprises paper or a nonwoven fabric.

19. The pouch of claim 17, wherein the breathable material comprises an uncoated nonwoven fabric.

20. The pouch of claim 17, wherein the top edges of the front and back sheet are unconnected to each other to define an access opening into the interior space of the pouch.

21. The pouch of claim 17, wherein the intermediate rupturable layer has a peel strength that is from about 0.75 to 3.5 lbs./in.

22. A sterilizable pouch comprising:
front and back sheets of a flexible film joined to each other along opposite side and bottom edges to define a pouch having an interior space for receiving an article therein, said flexible film being a multilayer film;
an opening formed in at least one of the front or back sheets, the opening for providing communication between an exterior environment of the pouch and said interior space;
a breathable material comprising an uncoated fibrous material that is impervious to microorganisms, but pervious to gases, overlying and covering said opening, and being directly joined to an outer surface of said front or back sheet with a continuous heat seal;
wherein the flexible film comprising the front or back sheet having said opening includes an outer heat seal layer defining an inner surface of the pouch, an outer layer defining an outer surface, and a layer having a peel feature such that the breathable material can be peelably removed from said outer surface without tearing of the breathable material, and wherein said peel feature comprises:
a) the outer layer of said flexible film that is comprised of a blend of polymeric materials that are selected so that a peel strength of the continuous heat seal, measured by ASTM test F88, is less than 700 N/m (4 lbs./in.); or
b) an intermediate rupturable layer disposed adjacent to the outer layer of said flexible film, said intermediate rupturable layer having a peel strength that is less than a peel strength of the continuous heat seal joining the breathable material to said outer surface, such that the breathable material can be removed by peeling the breathable material away from the outer surface of said front or back sheet which causes the intermediate rupturable layer to rupture along said heat seal; and wherein the outer layer has a lower melting threshold than the outer heat seal layer.

\* \* \* \* \*